United States Patent
Muccio

(10) Patent No.: US 11,541,228 B2
(45) Date of Patent: Jan. 3, 2023

(54) UPPER EXTREMITY BIOSLEEVE

(71) Applicant: AXIOBIONICS, Ann Arbor, MI (US)

(72) Inventor: Philip Muccio, Ypsilanti, MI (US)

(*) Notice: Subject to any disclaimer, the term of this patent is extended or adjusted under 35 U.S.C. 154(b) by 14 days.

(21) Appl. No.: 15/109,769

(22) PCT Filed: Jan. 5, 2015

(86) PCT No.: PCT/US2015/010189
§ 371 (c)(1),
(2) Date: Jul. 5, 2016

(87) PCT Pub. No.: WO2015/103557
PCT Pub. Date: Jul. 9, 2015

(65) Prior Publication Data
US 2016/0325090 A1    Nov. 10, 2016

Related U.S. Application Data

(60) Provisional application No. 61/923,465, filed on Jan. 3, 2014.

(51) Int. Cl.
*A61N 1/04* (2006.01)
*A61N 1/36* (2006.01)

(52) U.S. Cl.
CPC ......... *A61N 1/0484* (2013.01); *A61N 1/0452* (2013.01); *A61N 1/0456* (2013.01); *A61N 1/36003* (2013.01); *A61N 1/36014* (2013.01); *A61N 1/36021* (2013.01)

(58) Field of Classification Search
CPC ............... A61N 1/0452; A61N 1/0484; A61N 1/36003; A61N 1/36021
See application file for complete search history.

(56) References Cited

U.S. PATENT DOCUMENTS

| | | | | |
|---|---|---|---|---|
| 4,381,012 A | * | 4/1983 | Russek | A61N 1/0484 600/382 |
| 7,899,556 B2 | * | 3/2011 | Nathan | A61N 1/36003 607/144 |
| 2002/0032475 A1 | * | 3/2002 | Arbel | A61N 1/0456 607/149 |
| 2002/0058972 A1 | * | 5/2002 | Minogue | A61N 1/321 607/72 |
| 2003/0114893 A1 | * | 6/2003 | Nathan | A61N 1/0476 223/111 |
| 2005/0197599 A1 | | 9/2005 | Yu | |
| 2010/0130847 A1 | * | 5/2010 | Dunagan | A61B 5/0408 600/389 |
| 2011/0093035 A1 | * | 4/2011 | Moser | A61N 1/0484 607/48 |

(Continued)

FOREIGN PATENT DOCUMENTS

WO      2010027874 A2      3/2010
WO   WO 2010/027874   *   3/2010   ............... A61N 1/36

*Primary Examiner* — Eric D. Bertram
(74) *Attorney, Agent, or Firm* — Mindful IP PLLC

(57) ABSTRACT

The electrical stimulation garment includes an electrical stimulator, a flexible substrate, a plurality of electrical connectors, a plurality of electrodes and a plurality of locators. The electrical stimulation is applied to the body part by the electrical stimulator through the placement of the plurality of electrical connectors in contact with the plurality of electrodes to a prescribed area of the body part as identified by the plurality of locators.

9 Claims, 10 Drawing Sheets

(56) References Cited

U.S. PATENT DOCUMENTS

| | | | |
|---|---|---|---|
| 2012/0203156 A1* | 8/2012 | Dar | A61F 5/0106 602/5 |
| 2012/0330394 A1* | 12/2012 | Dar | A61F 5/0102 607/149 |
| 2013/0110220 A1* | 5/2013 | Brown | A61N 1/0452 607/149 |
| 2013/0158627 A1 | 6/2013 | Gozani et al. | |

* cited by examiner

UPPER EXTREMITY BIOSLEEVE

RELATED APPLICATIONS

This application claims the benefit of U.S. Provisional Patent Application No. 61/923,465, filed on Jan. 3, 2014. The entire contents of the above application are incorporated herein by reference.

FIELD

The present invention relates to electrical stimulation devices and, in particular, wearable electrical stimulation devices.

BACKGROUND

Electrical stimulation of muscles and nerves has been employed over the years to treat certain medical conditions. Typically an electrical stimulation device has a plurality of electrodes attached to a substrate that is configured to be worn by a patient. One difficulty is to properly and accurately locate the electrodes along the patient's body part to be treated.

Accordingly, there is room in the art for an electrical stimulation device that is configured to accurately locate the electrodes on the portion of the body part to be treated. Moreover, there is need for an electrical stimulation device or garment that incorporates electrodes that are easily removed from the garment and reattached at the proper location.

SUMMARY

In an aspect of the present invention, an electrical stimulation garment is provided. The electrical stimulation garment includes an electrical stimulator, a flexible substrate, a plurality of electrical connectors, a plurality of electrodes and a plurality of locators.

In accordance with an embodiment of the present invention, the electrical stimulator is configured to generate an electrical current sufficient to cause muscle contraction in a body part.

In accordance with another embodiment of the present invention, the flexible substrate is made of a Neoprene material.

In accordance with yet another embodiment of the present invention, the plurality of electrical connectors are in electrical communication with the electrical stimulator and releaseably attached to the substrate.

In accordance with yet another embodiment of the present invention, the plurality of electrodes are releaseably connected to the plurality of electrical connectors.

In accordance with yet another embodiment of the present invention, the plurality of locators are releaseably connected to the substrate to indicate the placement of the plurality of electrical connectors.

In accordance with yet another embodiment of the present invention, electrical stimulation is applied to the body part by the electrical stimulator through the placement of the plurality of electrical connectors in contact with the plurality of electrodes to a prescribed area of the body part as identified by the plurality of locators.

In accordance with still another embodiment of the present invention, the plurality of electrical connectors each includes a magnet.

In accordance with still another embodiment of the present invention, the plurality of electrodes each includes a magnet.

In accordance with still another embodiment of the present invention, the plurality of electrical connectors each includes a layer of velcro for releaseably attaching each of the plurality of electrical connectors to the substrate.

In accordance with still another embodiment of the present invention, the plurality of electrodes each includes a layer of velcro for releaseably attaching each of the plurality of electrodes to the substrate.

In accordance with still another embodiment of the present invention, the electrical stimulation garment further includes a plurality of lead wires for electrically interconnecting the plurality of electrical connectors with the electrical stimulator.

In accordance with still another embodiment of the present invention, the electrical stimulation garment further includes a plurality of channels for housing the plurality of lead wires.

In accordance with still another embodiment of the present invention, each of the plurality of channels is defined by an elongated flexible material attached to the substrate.

In accordance with still another embodiment of the present invention, the plurality of locators each includes a layer of Velcro for releaseably attaching each of the plurality of locators to the substrate to indicate the preferred placement of the plurality of electrical connectors.

Further features, advantages and areas of applicability will become apparent from the description provided herein. It should be understood that the description and specific examples are intended for purposes of illustration only and are not intended to limit the scope of the present disclosure.

DRAWINGS

The drawing described herein is for illustration purposes only and is not intended to limit the scope of the present disclosure in any way. In the drawing.

Figure 13:
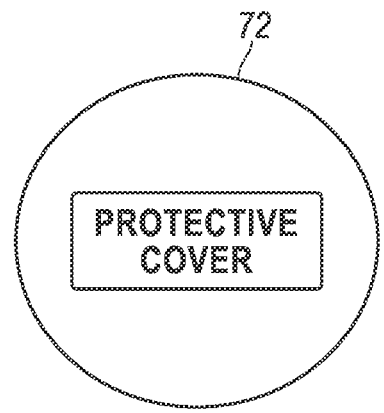
Figure 14:
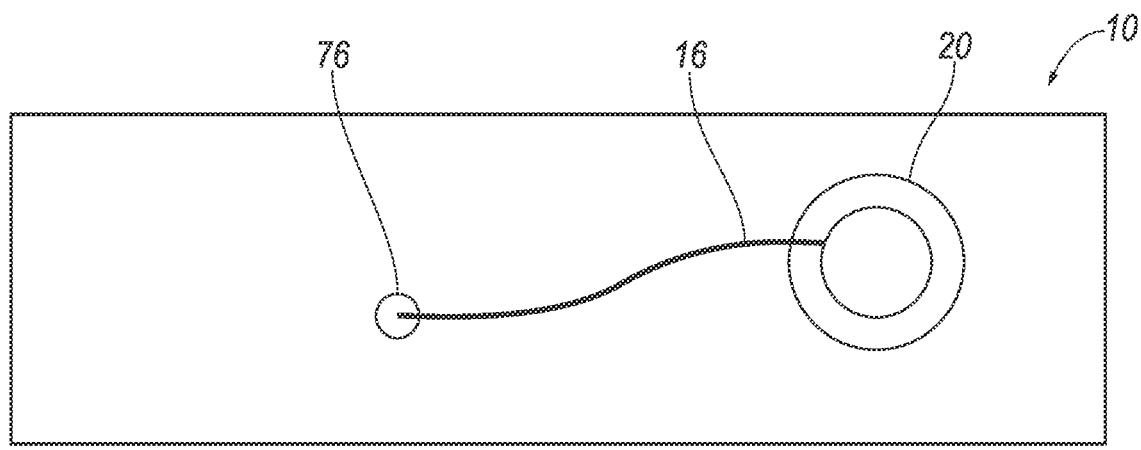

FIG. 13 is a perspective view of the protective cover of the electrical stimulation garment worn on the upper extremity to stimulate nerves and muscles, in accordance with the principles of the present invention; and FIG. 14 is a perspective view of the electrical stimulation garment illustrating the exit holes to allow the lead wires to pass from the lead wire channel, in accordance with the principles of the present invention.

Figure 15:
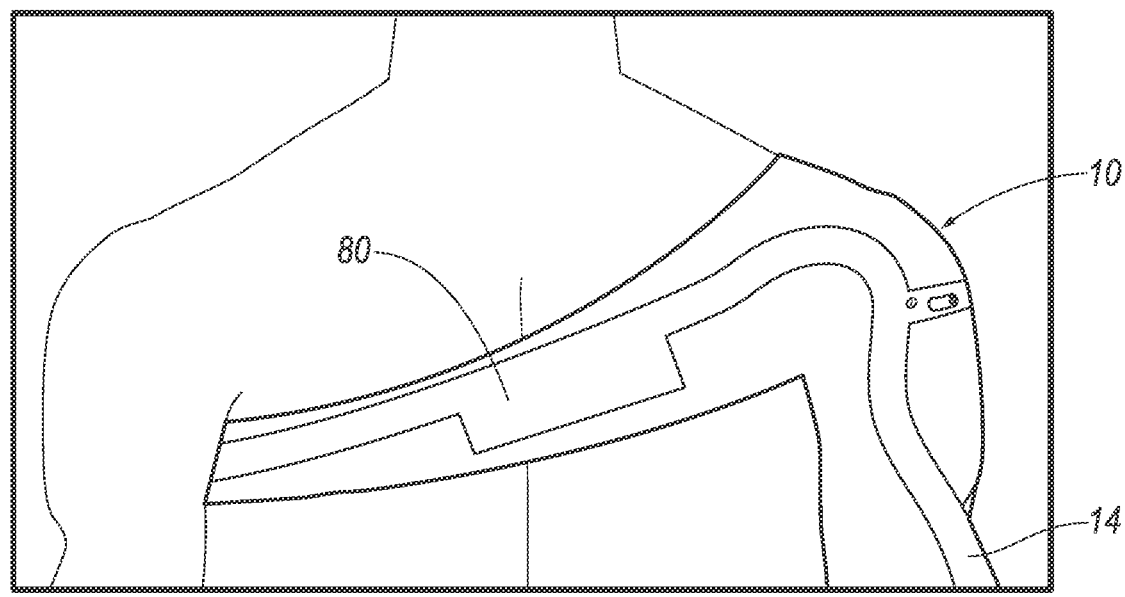

FIG. 15 is a back view of the electrical stimulation garment illustrating a lead wire pocket for housing the connectors between the lead wires and the lead wire cabling.

Figure 16:
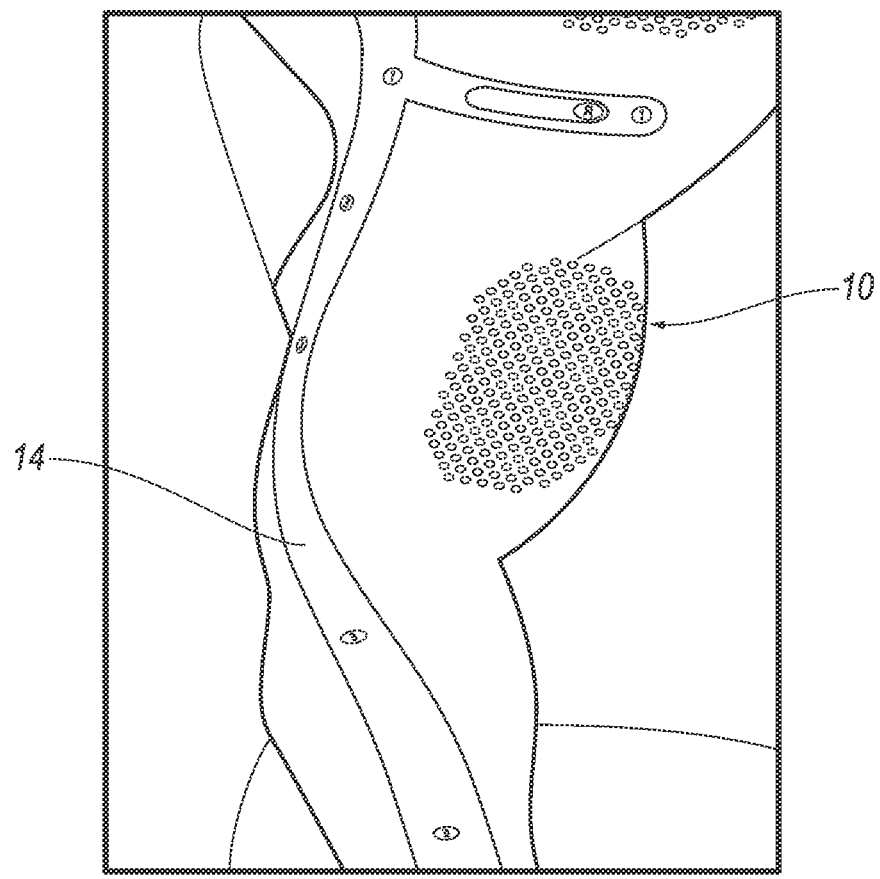

FIG. 16 is a perspective view of the electrical stimulation garment illustrating labels identifying which channel is stimulating the area of the arm or body part at the location of the label.

DETAILED DESCRIPTION

The following description is merely exemplary in nature and is not intended to limit the present disclosure, application, or uses.

Figure 1:
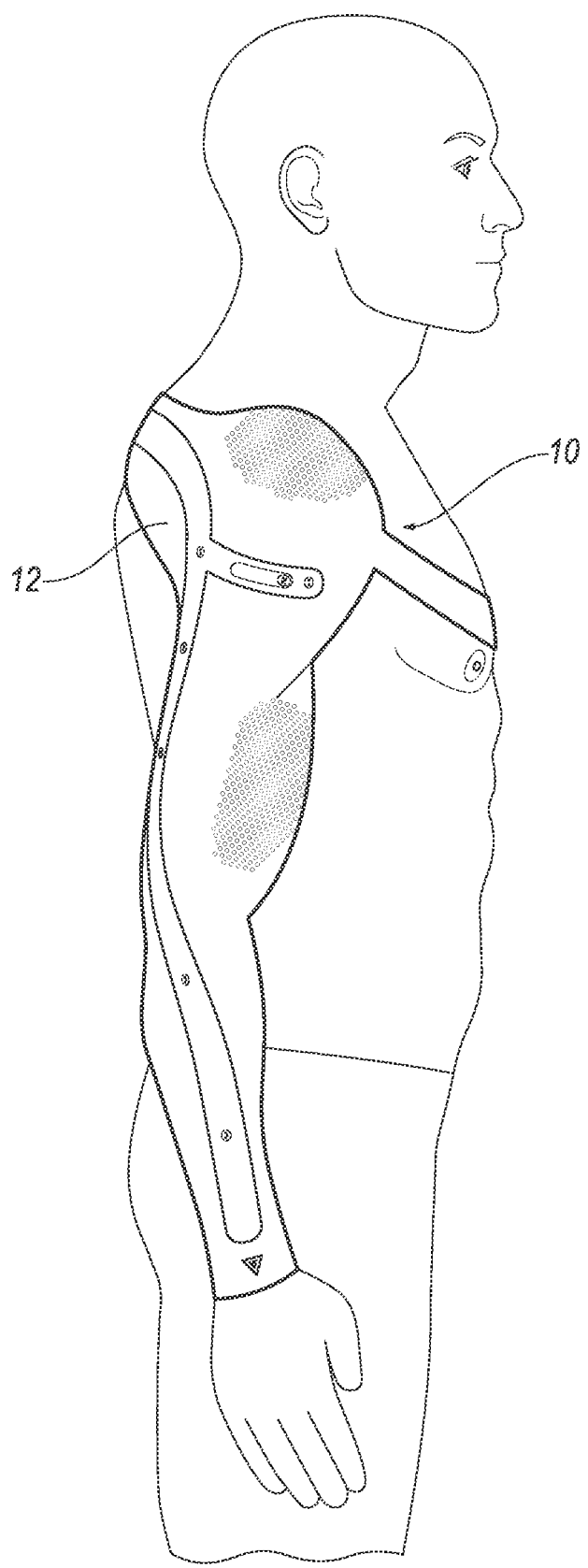
FIG. 1 is a perspective view of an electrical stimulation garment worn on the upper extremity to stimulate nerves and muscles, in accordance with the principles of the present invention.

Referring now to FIG. 1, a perspective view of an upper extremity BioSleeve (UE BioSleeve) 10 is illustrated. The UE BioSleeve 10 is an electrical stimulation garment worn on the upper extremity to stimulate nerves and muscles to produce various desirable medical outcomes such as relief of chronic pain, relaxation of muscle spasms, increased range of motion of joints, increased circulation to the limb, to reduce or eliminate subluxation of the shoulder joint, to re-educate muscles, to facilitate movement of the limb and to increase awareness of the limb. UE BioSleeve 10 utilizes a conventional electrical stimulator (not shown) connected to a plurality of electrodes through lead wires to transmit electrical current to the electrodes and thereby the body part to be stimulated.

The UE BioSleeve 10 is configurable depending on the area of the trunk and arm that needs to be covered for placement of electrodes.

In one embodiment of the present invention, the UE BioSleeve 10 is composed of a substrate 12 made of stretchable and flexible neoprene in which other components are sewn or fastened to, including neoprene loop material that mates with electrodes, domatrodes containing a stainless steel magnetic connector, lead wires, small hook dots used as domatrode locators and Velcro electrodes, as will be described hereinafter.

Figure 2:
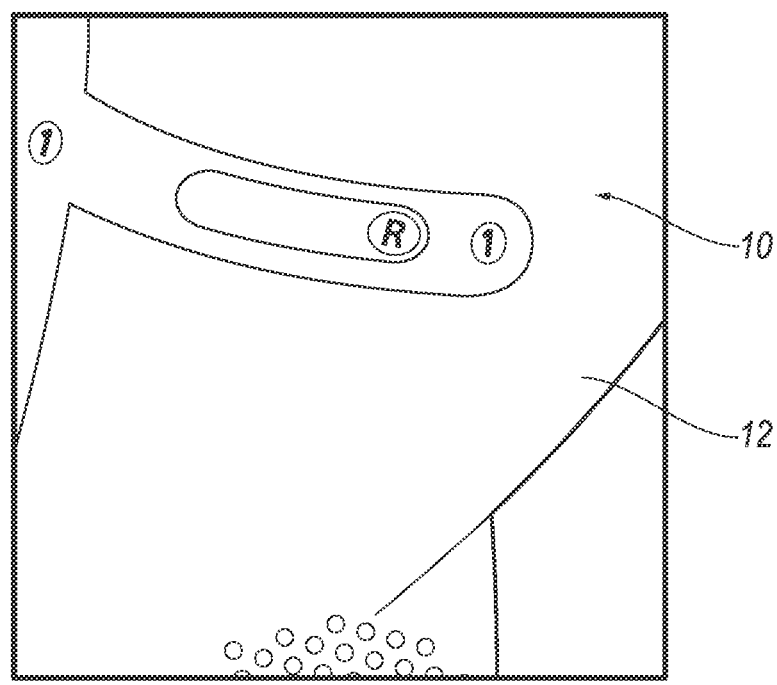
FIG. 2 is a perspective view of a portion of the electrical stimulation garment worn on the upper extremity to stimulate nerves and muscles, in accordance with the principles of the present invention.

In another embodiment of the present invention, substrate 12 is a flexible, Neoprene® material (S-foam) that serves as the support structure for the UE BioSleeve 10. The Neoprene® material of substrate 12 has bi-directional stretch so that the substrate 12 conforms to body contours around and over the limb or body part, as shown in FIG. 1 and FIG. 2 below. Substrate 12 is impervious to water and moisture and does not absorb moisture. Substrate 12 can be cut without fraying.

Figure 3:
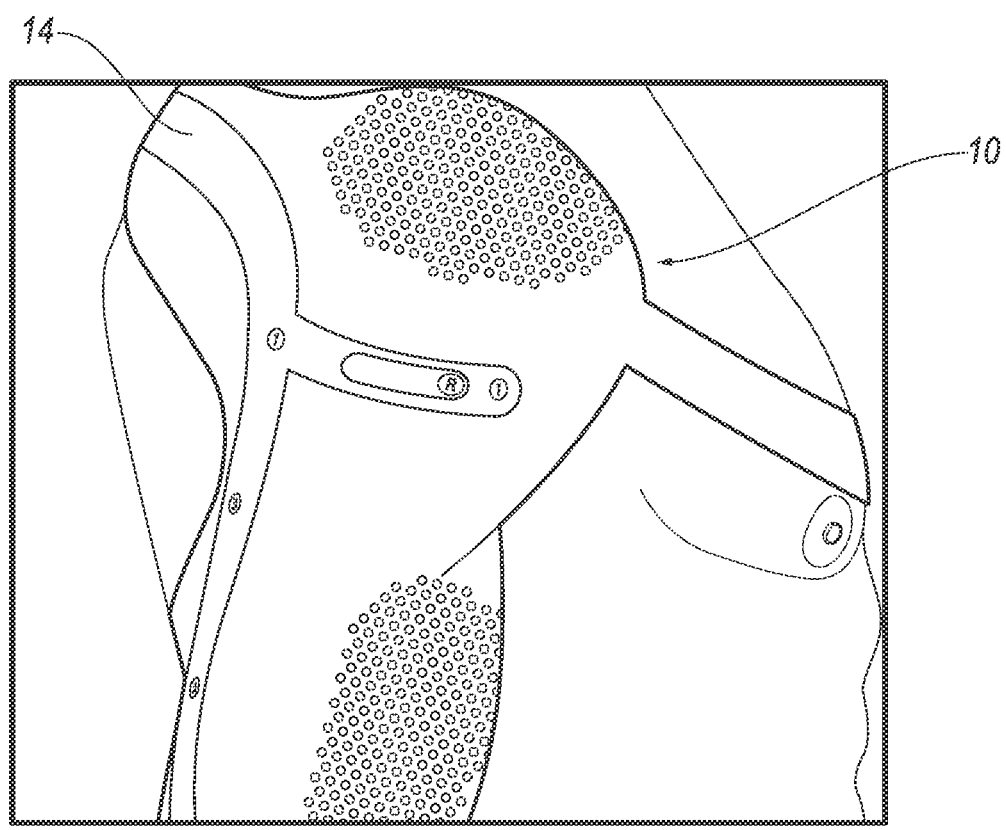
FIG. 3 is a perspective view of another portion of the electrical stimulation garment worn on the upper extremity to stimulate nerves and muscles and illustrating the wire channel, in accordance with the principles of the present invention.

Referring now to FIG. 3, a lead wire channel 14 is illustrated. Lead wire channel 14 is made of an elongated piece of Neoprene® S-foam material laid over top of the substrate 12 and fixedly attached to substrate 12 by stiches or other means. The lead wire channel 14 is designed to house the lead wires 16 (see FIG. 4) that carry electrical current from the pin lead connectors (of an electrical stimulator 17) on one end to the domatrode 20, stainless steel connector on the opposite end. The lead wire channel 14 protects the lead wires and prevents them from exposure.

Figure 4:
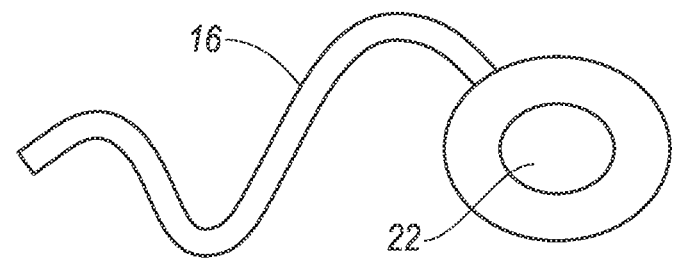
FIG. 4 is a perspective view of the electrical connector of the electrical stimulation garment worn on the upper extremity to stimulate nerves and muscles, in accordance with the principles of the present invention.
Figure 5:
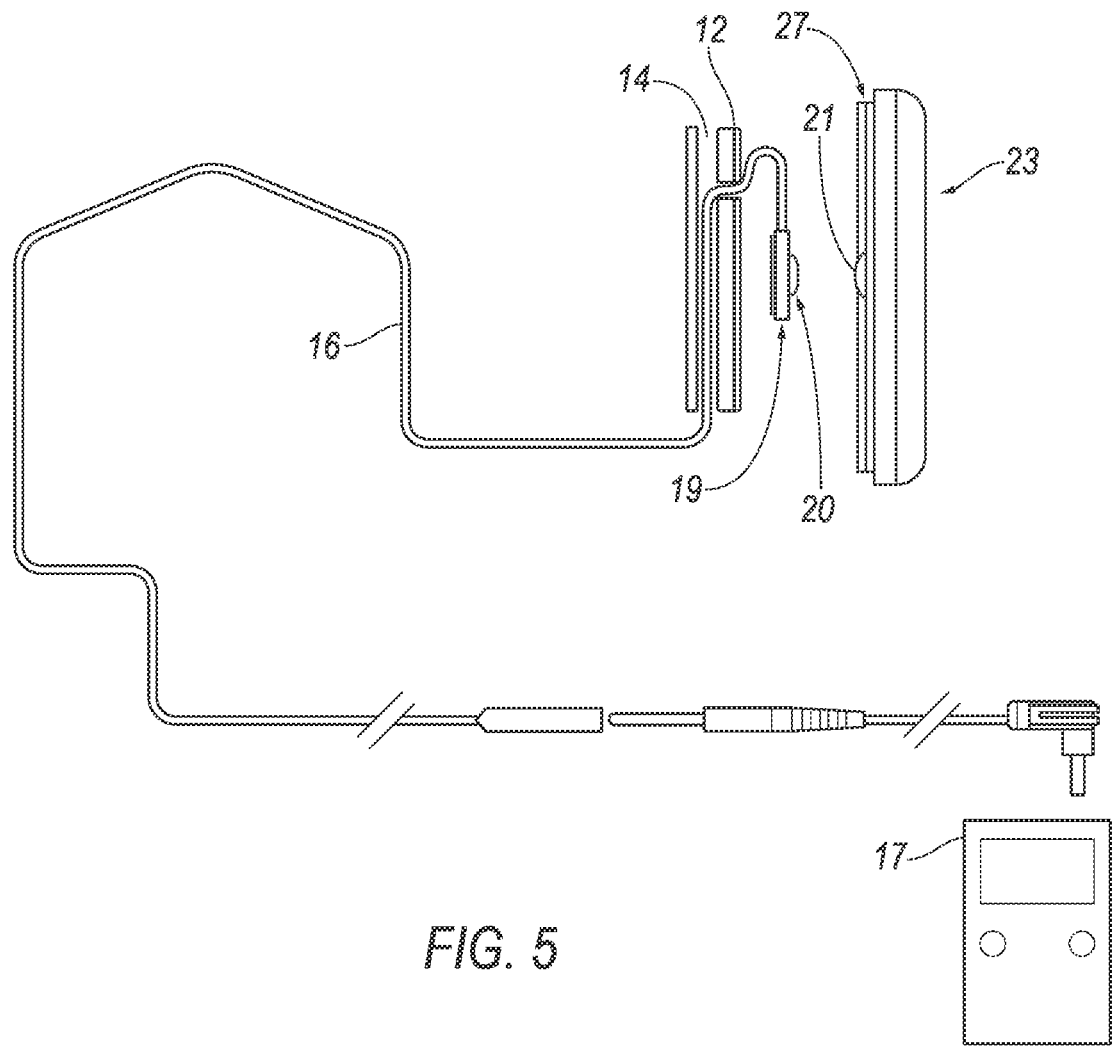
FIG. 5 is a perspective view of the electrode adjacent the electrical connector attached to the stimulator through a lead wire, in accordance with the principles of the present invention.

With specific reference to FIGS. 4 and 5, the domatrode 20 is an electrical connector configured to make electrical contact with a stainless steel connector or cap 21 on an electrode 23. The domatrode 20 connector has a metal cap 22 that contains a low-force magnet 22. The magnet 22 inside each cap 22 provides sufficient magnetic force to cause the domatrode 20 to couple to the electrode 23, yet weak enough to allow decoupling with ease by the user by hand when removing the electrode 23 from the garment. Once the domatrode 20 is connected to the electrode 23, an electrical current can pass through this connection. The underside of the domatrode 20 has a layer hook Velcro material 19 that mates with pile neoprene which holds the domatrode 20 to the UE BioSleeve 10.

Figure 6A:
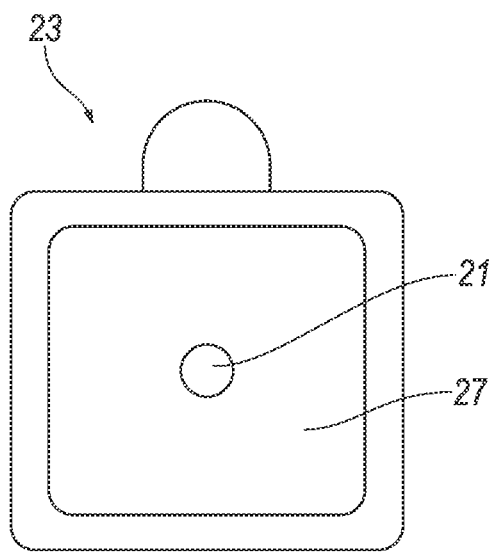
FIGS. 6A and 6B are a back side view and exploded view of the electrode, in accordance with the principles of the present invention.
Figure 6B:
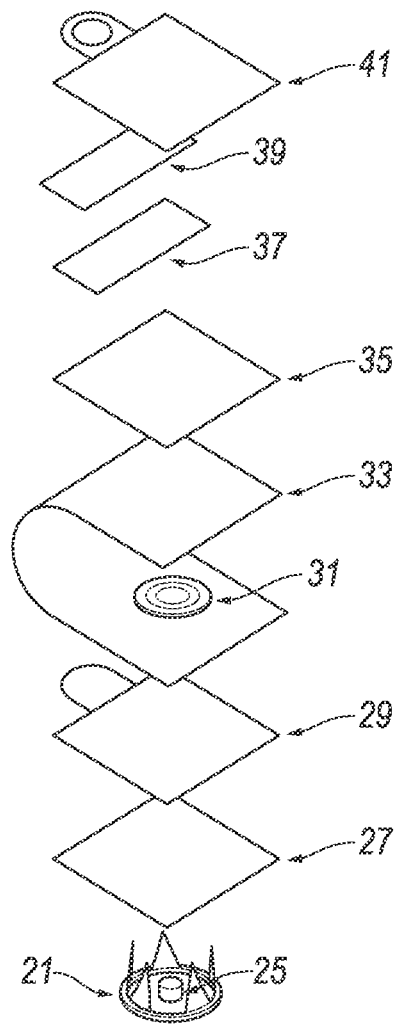

Referring now to FIGS. 6A and 6B, a front and exploded views of electrode 23 are shown, in accordance with the present invention. Electrode 23 includes a metal cap 21, magnets 25, a layer of hook Velcro material 27, a layer of vinyl spandex 29, a metal socket 31, a flexible folded layer of silver paper or silver ripstop fabric 33, a layer of light spandex 35, a layer of loop Velcro material 37, a layer of hook Velcro material 39, a layer of light spandex 41. The metal cap 21 has a plurality of metal tabs that are pressed through the intermediate layers and into the metal socket 31 thereby fastening and electrically connecting the metal cap 21 to the meal socket 31. Thus, the metal cap 21, the metal socket 31 and the flexible folded layer of silver paper 33 are in electrical communication. The layer of light spandex 41 contacts the patient's skin and allows the electrical current to pass from the metal cap 21 through to the body part to be stimulated. Each electrode 23, regardless of shape or dimension, includes the metal cap 21 that mates with the metal cap 22 on the domatrode 20. The perimeter of the electrode 23 is free of Velcro material so that the user can remove the electrode 23 from the sleeve 10 with very little force by grab and lift the electrode 23 from the sleeve 10.

Figure 7A:
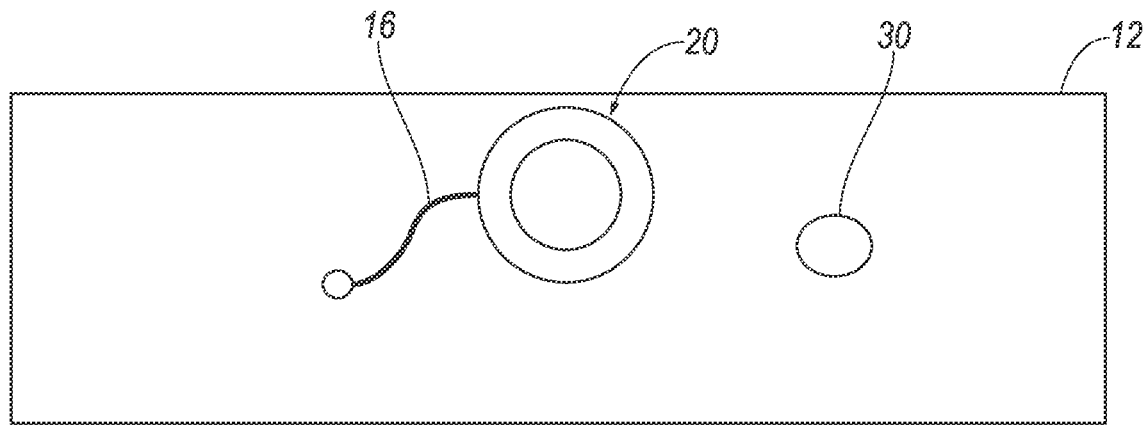
FIGS. 7A and 7B is a perspective view of the electrical connector or domatrode releaseably connected to the substrate adjacent the locator and over top of the locator, in accordance with the principles of the present invention.
Figure 7B:
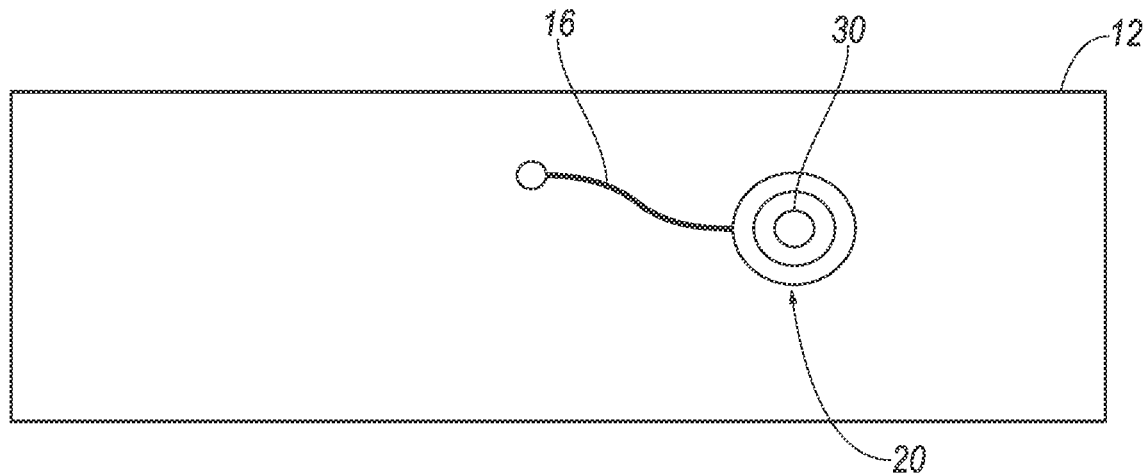

Referring now to FIGS. 7A and 7B, top views of domatrode 20 are shown releaseably attached to the substrate 12, in accordance with the present invention. Domatrodes 20 can be shifted to any position on the sleeve within a certain radius to maximize the possible locations for an electrode. A Velcro locator dot 30 is a piece of material (i.e. neoprene) in the shape of a dot and has a hook Velcro fastener that fastens to the neoprene substrate 12 to mark a preferred location of the domatrode 20. The Velcro locator dot pin points the location of where the clinician wants to place an electrode 23 (over the domatrode 20). When the sleeve 10 is configured to fit a particular patient, a clinician applies the sleeve 10 and places a chalk mark on the outside of the sleeve 10 where an electrode 23 should be placed. Once that is determined, a Velcro dot 30 is placed on the inside of the sleeve exactly opposite of where the clinician marked the sleeve 10. The domatrode 20 is placed over the Velcro dot 30. An electrode 23 is then connected to the domatrode 20 at the location of the Velcro dot 30, as shown in FIGS. 7A and 7B.

Figures 8A, 8B:
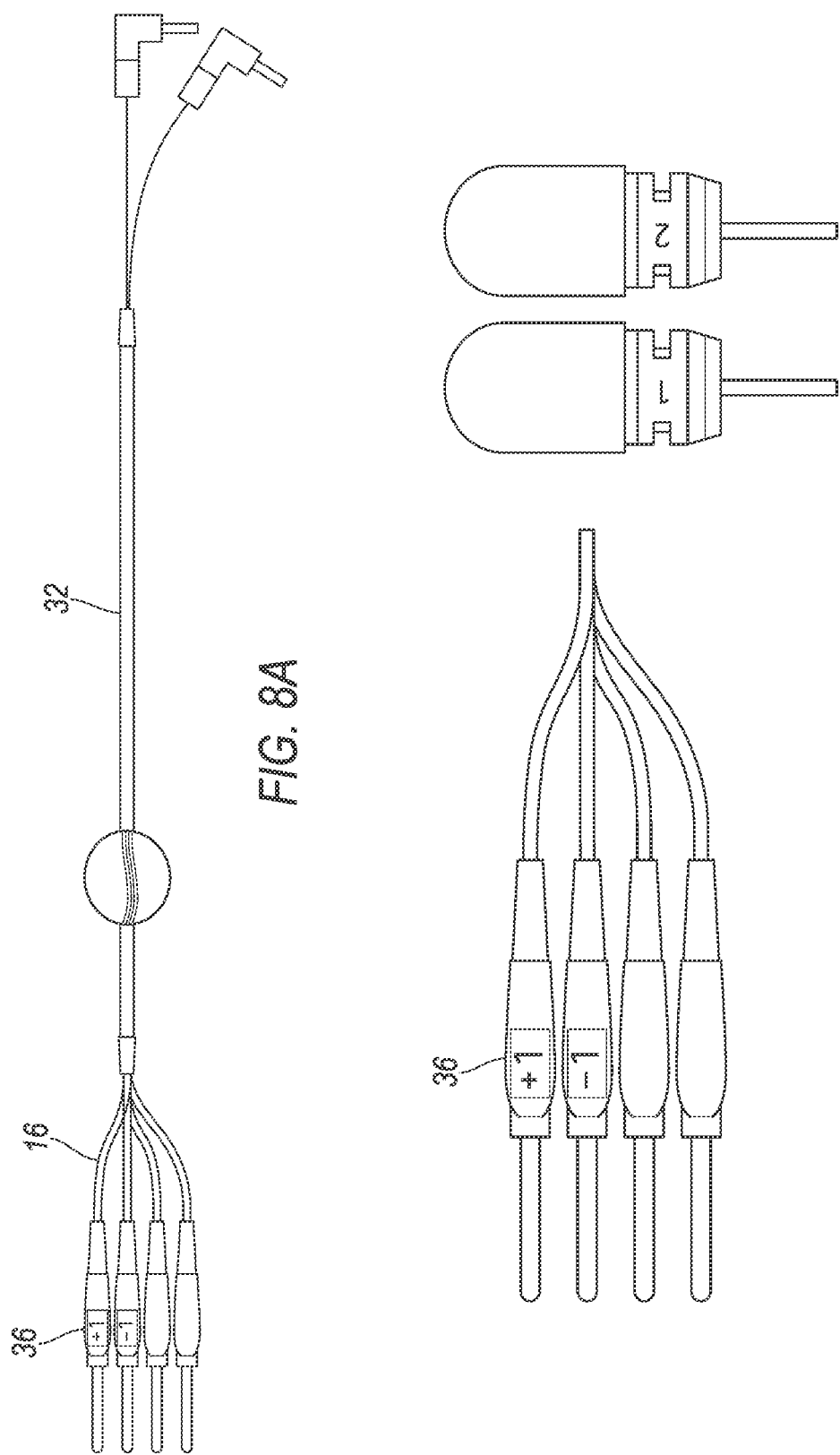
FIGS. 8A and 8B is a perspective view of the lead wires of the electrical stimulation garment, in accordance with the principles of the present invention.

Referring now to FIGS. 8A and 8B, perspective views of lead wires 16 are shown, in accordance with the present invention. Lead wires 16 are enclosed in a protective tubular weave material 32 to contain them and keep them organized. The connector end 36 of each lead wire 16 is labeled with its respective channel number so that the user is guided to insert the connector 36 into the correct receptacle on the electrical stimulator 17. This ensures that each channel of stimulation is delivered to the correct pair of electrodes.

Figure 9:
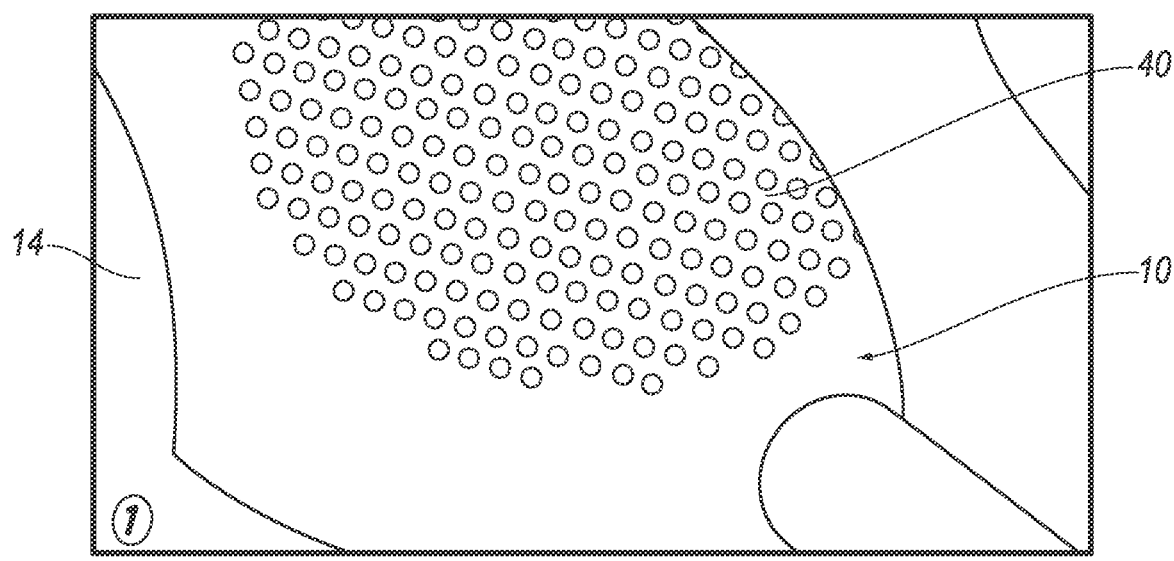
FIG. 9 is a perspective view of the ventilation areas of the electrical stimulation garment worn on the upper extremity to stimulate nerves and muscles, in accordance with the principles of the present invention.

Referring now to FIG. 9, a side view of the biosleeve 10 is shown, in accordance with the present invention. Additionally, the BioSleeve 10 has ventilated spandex areas 40 that are formed by cutting or punching holes in the neoprene material of the substrate 12, as illustrated in FIG. 9. Ventilated spandex areas 40 are strategically placed on the sleeve 10 to ventilate and cool the sleeve. Advantageously, the ventilated spandex areas 40 are placed over the radius of the shoulder joint to improve conformity and contour of the sleeve 10 over the shoulder.

Figure 10:
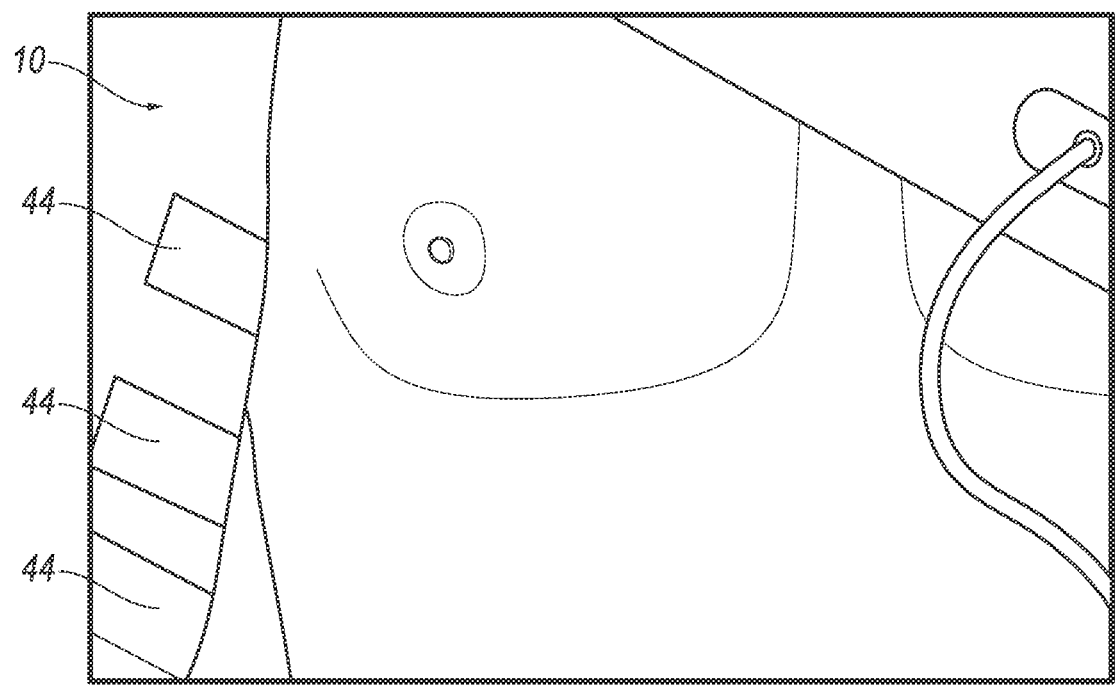
FIG. 10 is a perspective view of the Velcro closures or straps of the electrical stimulation garment worn on the upper extremity to stimulate nerves and muscles, in accordance with the principles of the present invention.

The sleeve 10 also includes Velcro closures or straps 44 (see FIG. 10) to accommodate reduction in muscle atrophy, swelling and to improve the fit of the sleeve 10.

Figure 11:
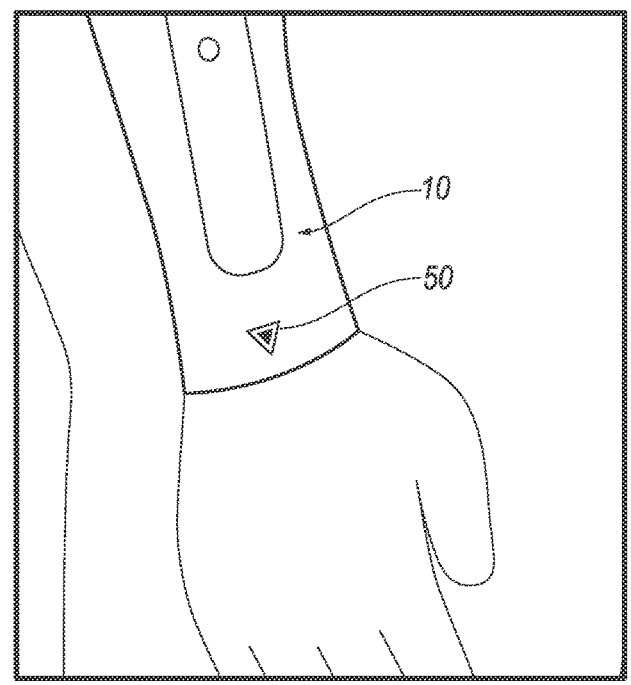
FIG. 11 is a perspective view of the pointers of the electrical stimulation garment worn on the upper extremity to stimulate nerves and muscles, in accordance with the principles of the present invention.

Pointers 50, as shown in FIG. 11, are used on the sleeve 10 at strategic locations to position the sleeve 10 on the arm or body part so that electrodes 23 accurately align with the muscle to be stimulated as the sleeve 10 is applied to the body part. If the sleeve 10 extends to the wrist, a label (pointer 50) is located at the center of the wrist pointing distally. A pointer 50 may also be added to the sleeve 10 pointing at the center of the cubital fold.

Figure 12:
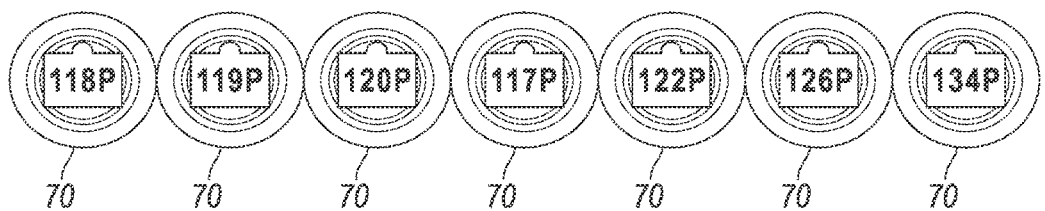
FIG. 12 is a perspective view of the electrode icons of the electrical stimulation garment worn on the upper extremity to stimulate nerves and muscles, in accordance with the principles of the present invention.

Electrode icons 70, as shown in FIG. 12, are fastened with hook Velcro to the neoprene substrate 12 material on the inside of the sleeve 10. The purpose of the electrode icon 70 is to orient the user so that the correct electrode is placed on the corresponding domatrode 20 and that the electrode is properly oriented on the sleeve 10.

A protective cover 72, as shown in FIG. 13, is fastened to the inside of the sleeve 10 over an unused domatrode 20 to protect the user from exposure to current from a domatrode 20 having no electrode 23. The protective cover is made of an electrical non-conductive material and has a layer of hook Velcro material that enables the protective cover to be releasably fastened to the substrate 12.

Exit holes 76, as shown in FIG. 14, are provided in the sleeve 10 to allow the lead wires 16 to pass from the lead wire channel 14 through to the inside of the sleeve 10.

A Lead Wire Pocket 80, as shown in FIG. 15, is provided for housing of the connectors between the lead wires 16 and the lead wire cabling. The pocket 80 is made large enough to receive one or more lead wire connectors without causing them to be crammed into a space too small. Entrance to the pocket 80 is possible for repair or to change a lead wire 16 or lead wire cable.

Each lead wire channel 14 is labeled, as shown in FIGS. 15 and 16, on the outside of the sleeve 10 so that the user knows which channel 14 is stimulating what area of the arm or body part. For example, channel 1 labeling is located over a first muscle group, channel 2 labeling is located over a second muscle group and channel 3 labeling is located over a third muscle group.

The description of the invention is merely exemplary in nature and variations that do not depart from the gist of the invention are intended to be within the scope of the invention. Such variations are not to be regarded as a departure from the spirit and scope of the invention.

What is claimed is:

1. An electrical stimulation garment comprising:
an electrical stimulator configured to generate an electrical current sufficient to cause muscle contraction in a body part;
a flexible substrate;
a plurality of electrical connectors in electrical communication with the electrical stimulator and releasably attached to the substrate;
a plurality of electrodes releasably connected to the plurality of electrical connectors, and wherein the plurality of electrodes each includes a layer of a hook and loop fastener for releasably attaching each of the plurality of electrodes to the substrate;
a plurality of electrode icons, each releasably attached to an inside surface of the flexible substrate, wherein each of the electrode icons helps a user orient one of the plurality of electrodes relative to one of the plurality of electrical connectors;
a plurality of locators, wherein each of the plurality of locators is releasably connected to the substrate and to one of the plurality of electrical connectors to indicate the placement of each of the plurality of electrical connectors on the substrate; and
whereby, electrical stimulation is applied to the body part by the electrical stimulator through the placement of the plurality of electrical connectors in contact with the plurality of electrodes to a prescribed area of the body part as identified by the plurality of locators.

2. The electrical stimulation garment of claim 1 wherein the plurality of electrical connectors each includes a magnet.

3. The electrical stimulation garment of claim 2 wherein the plurality of electrodes each includes a magnet.

4. The electrical stimulation garment of claim 1 wherein the plurality of electrical connectors each includes a layer of a hook and loop fastener for releasably attaching each of the plurality of electrical connectors to the substrate.

5. The electrical stimulation garment of claim 1 further comprising a plurality of lead wires for electrically interconnecting the plurality of electrical connectors with the electrical stimulator.

6. The electrical stimulation garment of claim 5 further comprising a plurality of channels for housing the plurality of lead wires.

7. The electrical stimulation garment of claim 6 wherein each of the plurality of channels is defined by an elongated flexible material attached to the substrate.

8. The electrical stimulation garment of claim 1 wherein the plurality of locators each includes a layer of a hook and loop fastener for releasably attaching each of the plurality of locators to the substrate to indicate the preferred placement of the plurality of electrical connectors.

9. The electrical stimulation garment of claim 1 further comprising a pointer printed on the flexible substrate for aligning the electrical stimulation garment relative to the body part.

* * * * *